United States Patent [19]

Stratbucker et al.

[11] 4,085,407
[45] Apr. 18, 1978

[54] DATA PLOTTER

[75] Inventors: Robert A. Stratbucker; John S. Hagood, both of Omaha, Nebr.

[73] Assignee: Health Technology Laboratories, Inc., Omaha, Nebr.

[21] Appl. No.: 681,138

[22] Filed: Apr. 28, 1976

[51] Int. Cl.² .................... G01D 9/30; A61B 5/04
[52] U.S. Cl. .................... 346/33 ME; 128/2.06 V; 346/23; 346/50; 346/76 R
[58] Field of Search ............... 346/76 R, 49, 50, 34, 346/33 ME, 23; 128/2.06 V, 2.06 G

[56] References Cited

U.S. PATENT DOCUMENTS

| | | | |
|---|---|---|---|
| 3,039,101 | 6/1962 | Perdue | 346/23 X |
| 3,085,132 | 4/1963 | Innes | 178/30 |
| 3,333,580 | 8/1967 | Fawcett | 346/33 ME X |
| 3,951,247 | 4/1976 | Montanari | 197/1 R |
| 3,975,742 | 8/1976 | Kelley | 346/76 R |

*Primary Examiner*—Joseph W. Hartary
*Attorney, Agent, or Firm*—McCaleb, Lucas & Brugman

[57] ABSTRACT

A data plotter for use in a multi-channel chart recorder operable to record time-variant analog scalar components of vector data signals on a moving recording medium. The data plotter comprises stationary printing means, preferably a thermal print head, for plotting vectors and other data derived from sampled scalar components as an aid in the interpretation of their analog traces.

13 Claims, 13 Drawing Figures

DATA PLOTTER

BACKGROUND OF THE INVENTION

1. Field of the Invention

This invention relates in general to chart recorders, and more particularly, to a data plotter for use therein.

2. Description of the Prior Art

Well-known multiple channel strip chart recorders have been provided for recording time-variant analog data by means of ink or heat pens in contact with a moving paper strip or other recording medium. Such recorders are frequently employed to record analog data comprising time-variant scalar or magnitude components of vector data signals having both magnitude and direction. Along with the recording of such scalar data, it is frequently desirable to simultaneously plot or record vector information and other data derived from the scalar data as an aid in the interpretation of their analog traces.

For example, in the clinical interpretation of electrocardiographic information, which includes analog traces of time-variant scalar components of vector heart potentials or voltages, it is a significant aid to diagnostic accuracy to observe plots of the voltage vectors and other data derived from the scalar data components along with the standard scalar electrocardiogram. In the cardiac cycle, the heart generates time-variant voltages or potentials which are vector quantities having both magnitude and direction. During each heart cycle, these voltages sweep through a three-dimensional pathway called a vector loop, initially increasing from zero value while being directed toward one side of the heart, then reaching a maximum, and then decreasing back to zero value while directed toward the opposite side of the heart. A standard electrocardiogram separately records along three mutually perpendicular axes only the scalar components or magnitudes of these three-dimensional time-variant vector potentials. However, observation of the planar vector loops is extremely helpful in the interpretation of the standard electrocardiogram data. An analysis of the heart vector potentials and the interpretation of their vector loops can be found in *Clinical Vectorcardiography*, by Chou, Helm and Kaplan, published by Grune and Stratton of New York and London in 1974.

Although available, instrumentation for recording or displaying such vector loops and other derived data is extremely expensive and cumbersome to operate in a clinical setting. Such equipment typically involves the photography of vector loops while they are being displayed on a cathode ray screen, and requires an expensive camera, a hooded cathode ray tube, electronic amplifiers and a power supply. Furthermore, it is difficult for the operator, while viewing the screen through the hood, to correlate the briefly displayed vector loops with the conventional electrocardiogram tracings.

Although chart recorders such as those disclosed in U.S. Letters Pat. No. 3,840,878, which issued Oct. 8, 1974 to Houston and Wilson, have been provided with print heads movable across the chart paper for recording digital characters and data, applicants are unaware of any self-contained chart recorder having a stationary printing device capable of printing or plotting data derived or computed from sampled input data.

SUMMARY OF THE INVENTION

The present invention is a simple and convenient solution to this problem and provides a relatively inexpensive data plotter for use within a self-contained chart recorder for printing, on a single document, not only the time-variant analog components of input data signals but also data derived therefrom.

In general, the present invention comprises a data plotter having a printing means, preferably a thermal print head, mounted in stationary relation to the recorder. An integrated circuit microcomputer is operable to process a time sample of the input data signals and to control the printing means for plotting or printing mathematically derived quantities. The processed data appears on the same sheet of substantially continuously moving strip chart recording paper for convenient correlation with the analog tracings.

Accordingly, it is an important object of the present invention to provide a device for plotting derived digital data along with analog time-variant data recorded by a chart recorder.

It is another important object of this invention to provide a data plotter employing a relatively inexpensive microcomputer for deriving or computing digital data from input data signals.

Yet another important object of this invention is to provide a data plotter which is compact and readily adaptable for use in a multi-channel chart recorder.

A further important object of this invention is to provide a data plotter having a printing means mounted in stationary relation to a chart recorder and being operable to print, on a substantially continuously moving strip chart, digital data derived from sampled input data for convenient correlation with the analog traces of the input data.

Still another important object of this invention is to provide a device for plotting vector loops of cardiac voltages as an aid in the clinical interpretation of a standard electrocardiogram.

Numerous other objects and advantages of the present invention will be apparent from the following description, which, when taken in conjunction with the accompanying drawings, discloses a preferred embodiment of the invention.

DESCRIPTION OF THE PREFERRED EMBODIMENT

Figure 1:
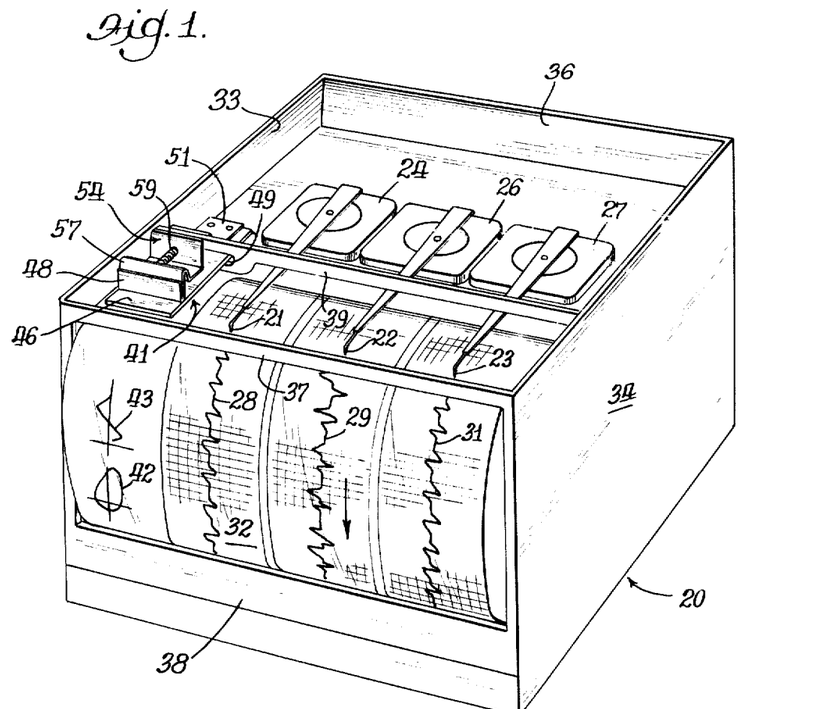
FIG. 1 is a perspective view of a multi-channel electrocardiogram recorder having a data plotter of the present invention for printing derived data alongside the analog electrocardiogram traces.

With particular reference to FIG. 1, reference numeral 20 indicates a three-channel chart recorder having analog pens 21, 22 and 23 controlled by pen motors 24, 26 and 27 for recording time-variant traces 28, 29 and 31, respectively, on a moving strip chart paper or recording medium 32. The pen motors 24, 26 and 27 are connected to known electrical control circuitry (not shown) which receives time-variant analog data and controls corresponding movement of the pens 21, 22 and 23 in a direction transverse to the direction of paper movement, which is indicated by the large arrow in FIG. 1.

The preferred embodiment of the present invention will be described and illustrated in conjunction with a chart recorder operable to provide a standard electrocardiogram, which indicates three time-variant scalar components of cardiac heart voltages or potentials measured along three mutually perpendicular axes conventionally designated the X, Y and Z axes.

Recorder 20 includes a pair of side plates 33, 34 (FIG. 1) joined to a rear plate 36, an upper front bar 37, a lower front bar 38 and an upper horizontal support 39 which mounts a printing means 41 in stationary relation to the recorder. Printing means 41 is operable to plot or print on the recording paper 32 one or more vector loops typified by reference numeral 42 and other data 43 derived or computed by a microcomputer circuit, in a manner to be described, from the analog data recorded by the pens 21, 22 and 23. The printing means 41 plots the derived data alongside the analog traces 28, 29 and 31 as a convenient aid in their interpretation.

The microcomputer comprises relatively inexpensive minature integrated circuit chips which are conveniently located in a package (not shown) suitably secured to the outside of the recorder 20. The microcomputer or data processing unit comprises a commercially available microprocessor, such as Model 8080 manufactured by the Intel Corporation of Santa Clara, California, and compatible input and output circuits. Since the data processing unit is well-known and commercially available, its physical details will not be described herein. However, the basic electrical block diagram of the electronic circuitry for controlling printing means 41 is found in FIG. 7 and will be described later.

Figure 2:
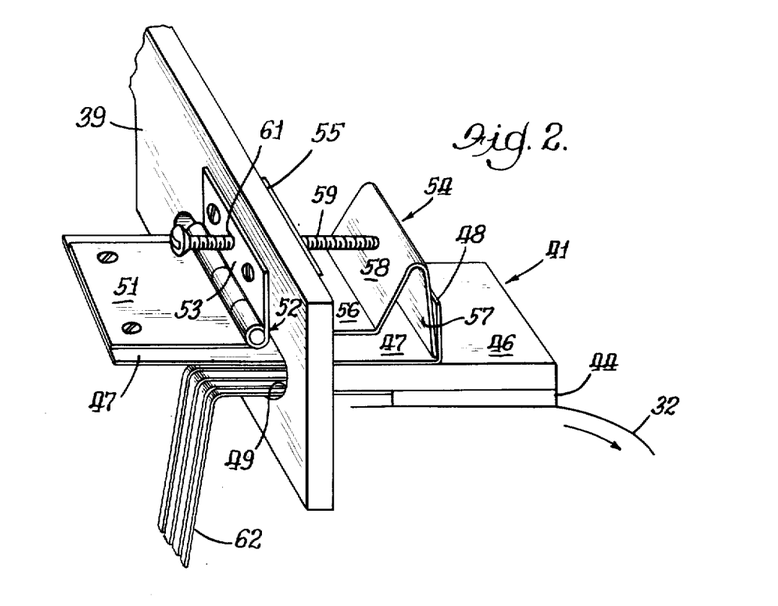
FIG. 2 is an enlarged perspective view taken from the left-hand side of FIG. 1, with parts broken away, showing the details of a thermal print head used in the data plotter illustrated in FIG. 1.

With reference to FIG. 2, printing means 41 comprises a known print head 44 and mounting means for maintaining printing contact between the print head and the paper 32. The print head 44 is secured to a substrate block 46 which is connected to one end of a horizontal metal mounting plate 47 having an upwardly extending end catch 48. Plate 47 extends rearwardly through an aperture 49 in the cross bar 39, and the rear end of plate 47 is suitably fastened to one plate 51 of a hinge 52 having another plate 53 suitably secured to the rear side of the cross bar. The hinge 52 is operable to pivotally support the plate 47 in order to effect vertical adjustment of the print head 44 with respect to the paper 32.

A spring means generally indicated by reference numeral 54 and preferably made of brass, phosphor-bronze or berrylium-copper alloys includes a vertical plate 55 secured to the front of cross bar 39, a horizontal portion 56 integrally formed with an inverted V-shaped end having a front leg 57 in contact with the inside edge of catch 48 and a rear leg 58 in contact with the end of an adjustment screw 59 threadedly disposed within a hole 61 in the cross bar. As the adjustment screw 59 is rotated forwardly relative to the cross bar 39, screw contact with the rear leg 58 forces the front leg 57 downwardly, thereby urging plate 47, substrate 46 and the print head 44 closer to the paper 32. Adjustment of the screw 59 insures printing contact between the print head 44 and the paper 32.

In the preferred embodiment of the present invention, the analog pens preferably comprise electrically operated heating elements which release encapsulated ink on thermosensitive paper 32 along their traces. The print head 44 is preferably a thermal print head of known design having a two inch span of 128 selectively energizable resistive printing elements spaced transversely to the longitudinal axis of the paper 32. These printing elements are connected to an energizing matrix of column and row conductors 62 (FIG. 2) which in turn are connected to the microcomputer output circuitry. When such a resistive element is energized, it releases encapsulated ink at its point of contact with the paper 32, thereby printing a dot. Thus, as the paper is moved by its known drive means (not shown), the analog pens 21, 22 and 23 record time-variant analog data traces and the selectively energizable printing elements of the print head 44 plot or print digital data alongside the analog traces 28, 29 and 31 in the margin of the paper 32 for convenient trace and plot correlation.

Figure 3:
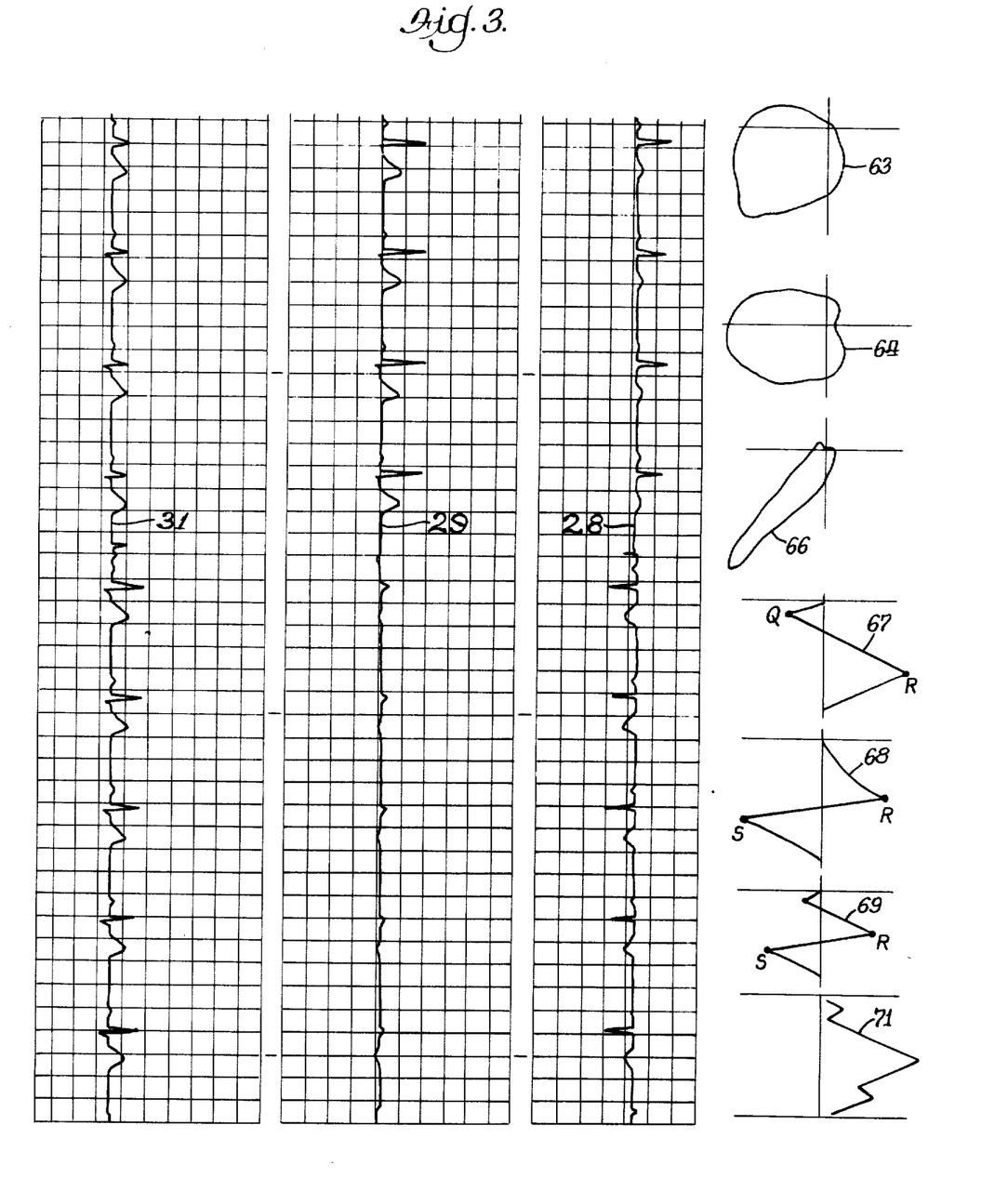
FIG. 3 illustrates a sample of a typical output document produced by the recorder of FIG. 1, containing both the analog traces of the three time-variant scalar components of cardiac voltages along with plots of derived vector loops and plots of the sampled data.

FIG. 3 illustrates a sample of a typical segment of the output of recorder 20. As an aid in the interpretation of the analog traces 28, 29 and 31, the printing means 41 is operable to simultaneously print or plot in sequence, in the margin of continuously moving paper 32, the following data derived from the time-variant scalar components of vector data signals: an X versus Y vector loop 63 taken along the frontal heart plane, an X versus Z vector loop 64 taken along the horizontal plane, a Z versus Y vector loop 66 taken along the sagittal plane, an X versus time plot 67, a Y versus time plot 68, a Z versus time plot 69 and a plot 71 of the vector magnitude versus time. Since the vector loops 63, 64 and 66 are derived from sampled scalar data, plots 67, 68, 69 and 71 of the sampled data indicate whether they are representative samples. These seven plots are produced for the heart voltages occurring during each cardiac cycle. As will be explained, the printing means 41 also prints reference axes for these derived data foregoing plots. The data plotter of the present invention is alternatively operable to print on discontinuously moving paper in a manner to be described.

It should be noted that FIG. 3 illustrates curves fitted to the dots produced by the printing means 41. Depending upon the number of printing elements, various degrees of printing resolution will be obtained, but it is sufficient for diagnostic purposes to plot the vector loops and other derived data with a print head having 64 printing elements per inch.

The cyclical ventricular complex of primary diagnostic importance is conventionally designated the QRS complex having points Q, R and S, which are marked on plots 67, 68 and 69 in FIG. 3. The initial deflection below the isoelectric line is called the Q point or portion, the first rise or voltage deflection above the isoelectric line is called the R point and the terminal deflection S refers to the last point below the isoelectric line from which the voltage decreases back to zero.

Figure 4:
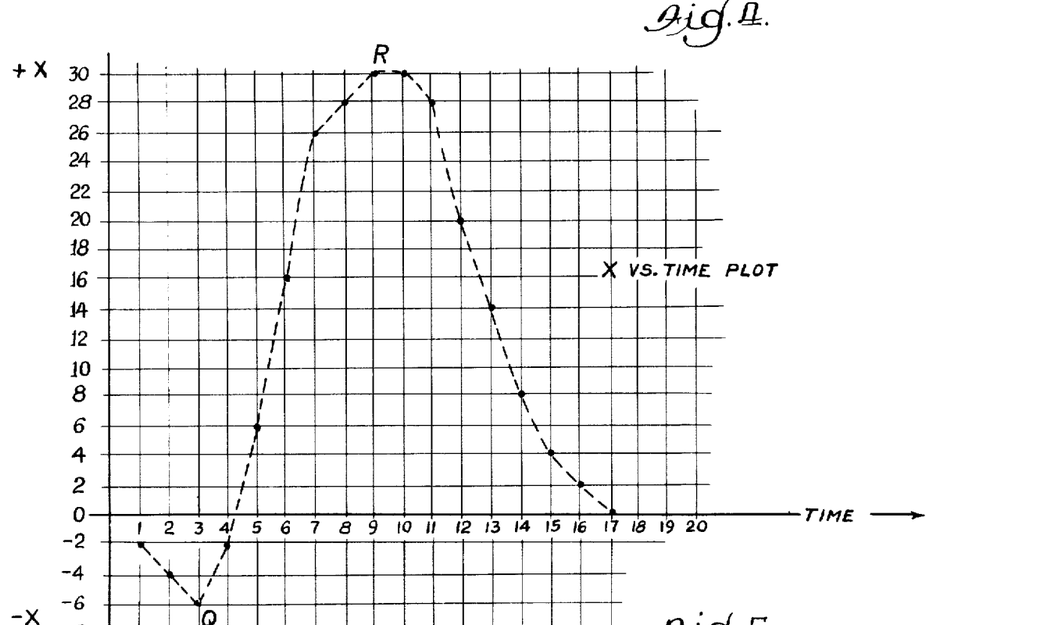
FIGS. 4 and 5 are typical plots of two time-variant scalar components of heart potentials occurring during a cardiac cycle.
Figure 5:
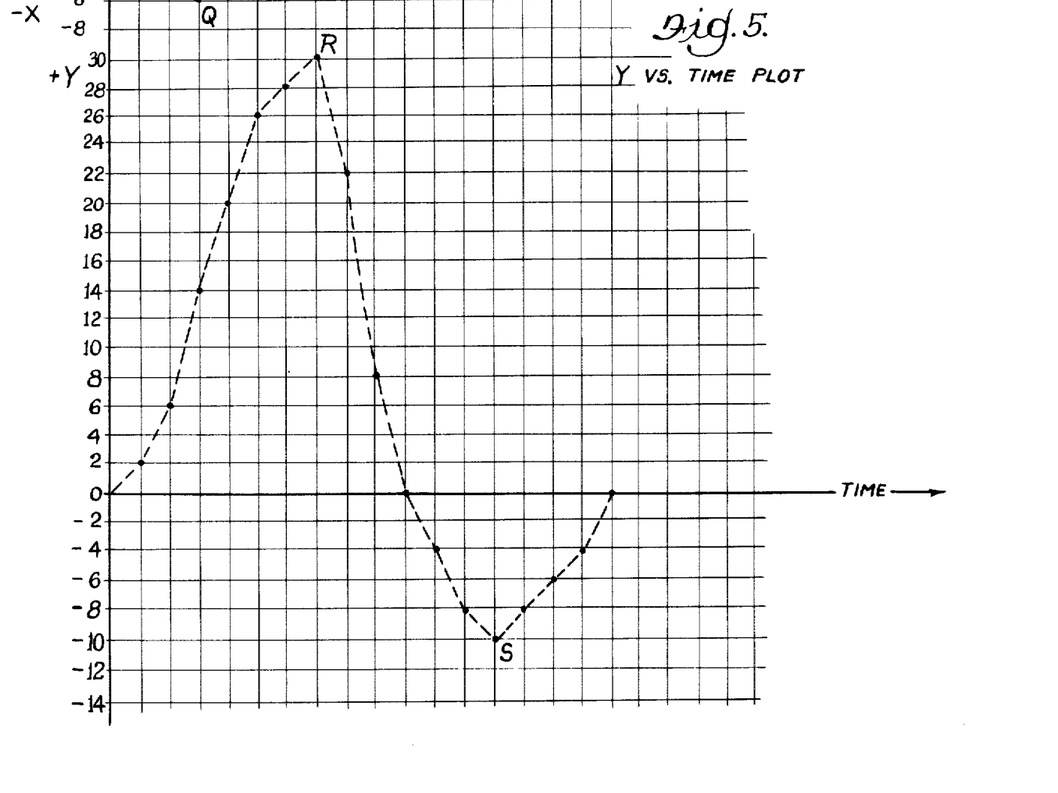
Figure 6:
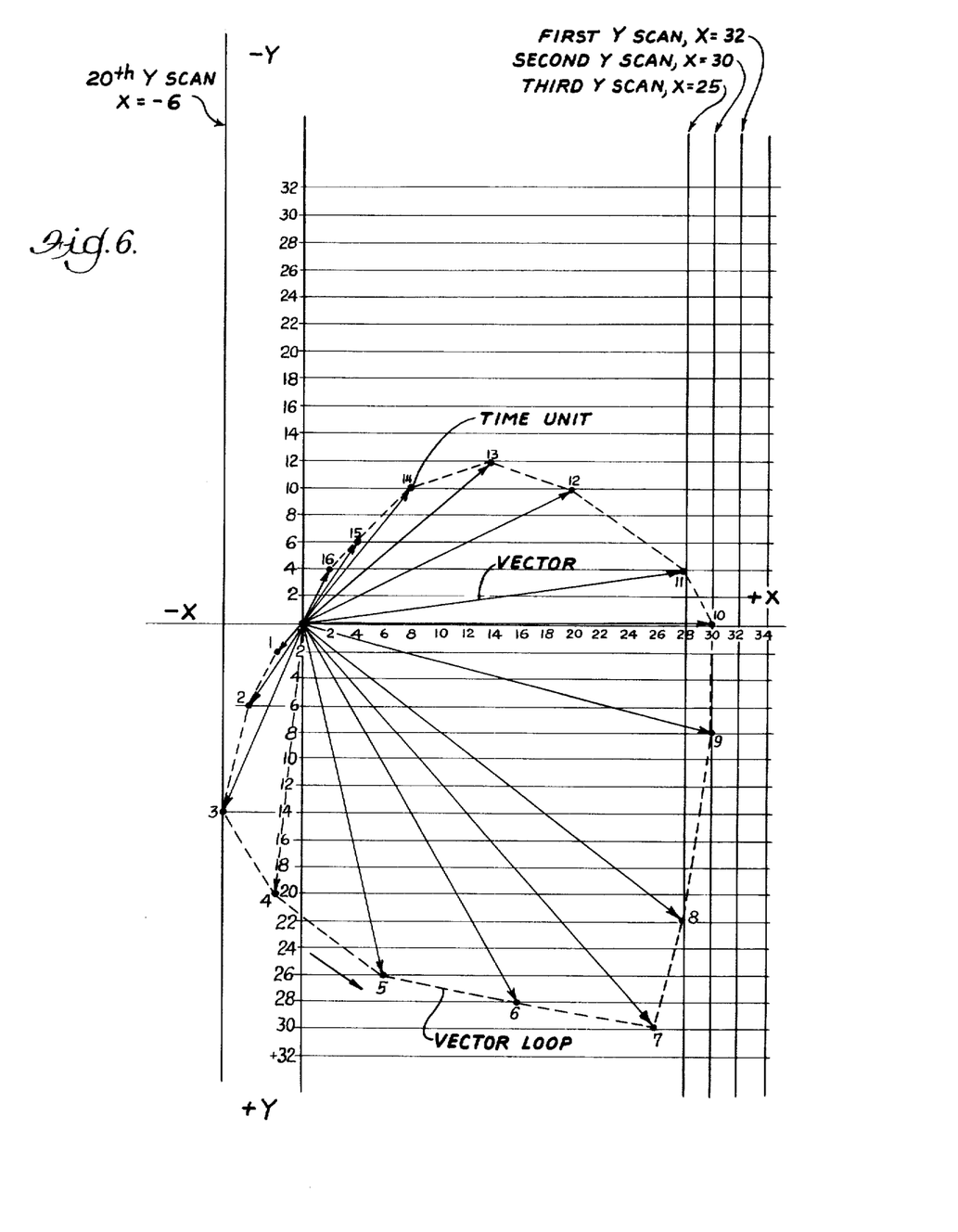
FIG. 6 is a planar vector loop derived from the data illustrated in FIGS. 4 and 5 for the purpose of illustrating the process of deriving a vector loop from its related scalar components as employed in the present invention.

Before the microprocessor program is described, it will be helpful to examine a typical example of an X versus time plot of FIG. 4, a Y versus time plot of FIG. 5 and the process by which the X versus Y vector loop of FIG. 6 is derived from the data of FIGS. 4 and 5. For this example, the time-associated X and Y values for 17 time intervals each having a 20 millisecond duration are charted below as time-sequential series of values:

| TIME UNIT | X VALUE | Y VALUE |
|---|---|---|
| 1 | −2.0 | 2.1 |
| 2 | −4.2 | 6.0 |
| 3 | −6.3 | 14 |
| 4 | −2.1 | 20 |
| 5 | 6.0 | 26 |
| 6 | 16 | 28 |
| 7 | 26 | 30 |
| 8 | 26 | 22 |
| 9 | 30 | 8.1 |
| 10 | 30 | 0.2 |
| 11 | 28 | −4.1 |
| 12 | 20 | −10 |
| 13 | 14 | −12 |
| 14 | 8.2 | −10 |
| 15 | 4.0 | −6.2 |
| 16 | 2.1 | −4.0 |
| 17 | 0.0 | 0.0 |

The plots of X versus time (FIG. 4) and Y versus time (FIG. 5) were made directly from the above chart of digital data derived from a time sample of electrocardiogram data.

In the operation of the microprocessor used in the present invention, after the sampled data is stored as indicated by the above chart and converted into integer form, one set of data, called the independent variable data, the X data in this example, must be arranged as a numerically ordered series of values. The Y or dependent variable data must then be sorted so that the time-associated values of Y data can be identified for each value of X data. This sorting procedure is accomplished by the microprocessor in a manner to be described, and, for the present example, the result is shown in the following data array table:

| SCAN NUMBER | X VALUE | TIME-ASSOCIATED VALUE OF Y |
|---|---|---|
| 1 | 32 | — |
| 2 | 30 | 0,8 |
| 3 | 28 | −4,22 |
| 4 | 26 | 30 |
| 5 | 24 | — |
| 6 | 22 | — |
| 7 | 20 | −10 |
| 8 | 18 | — |
| 9 | 16 | 28 |
| 10 | 14 | −12 |
| 11 | 12 | — |
| 12 | 10 | — |
| 13 | 8 | −10 |
| 14 | 6 | 26 |
| 15 | 4 | −6 |
| 16 | 2 | −4 |
| 17 | 0 | 0 |
| 18 | −2 | 2,20 |
| 19 | −4 | 6 |

In order to print the vector loop shown in FIG. 6, the paper 32 will move relative to the printing elements in increments corresponding to value variations in the X or independent variable data. The data processing unit will actuate the selectively energizable printing elements corresponding to the one or more Y or dependent variable data values time-associated with each value of X or independent variable data. With reference to FIG. 6, the first scan corresponds to an X value of 32, for which there are no associated Y values, as indicated in the above charts. In the second scan, for the X value of 30, there are two time-associated values of Y, 0 and 8. The scanning and printing process is repeated until the complete vector loop is plotted. It will be noted that −Y is plotted upward by convention, and, in the present invention, the scanning is performed for X values varying from +32 to −32. For cross reference, the time units marked on each abscissa in the horizontal time scales of FIGS. 4 and 5 appear adjacent to the points plotted in FIG. 6, which also shows the voltage vectors drawn to each of these points. The locus of vector heads, the vector loop, indicates that during the illustrated cardiac cycle, the frontal plane heart voltages increased from zero, while being directed toward the lower left-hand or third quadrant, then reached their maximum value at the lower right-hand or fourth quadrant, and then decreased back to zero while in the upper right-hand or first quadrant.

Figure 7:
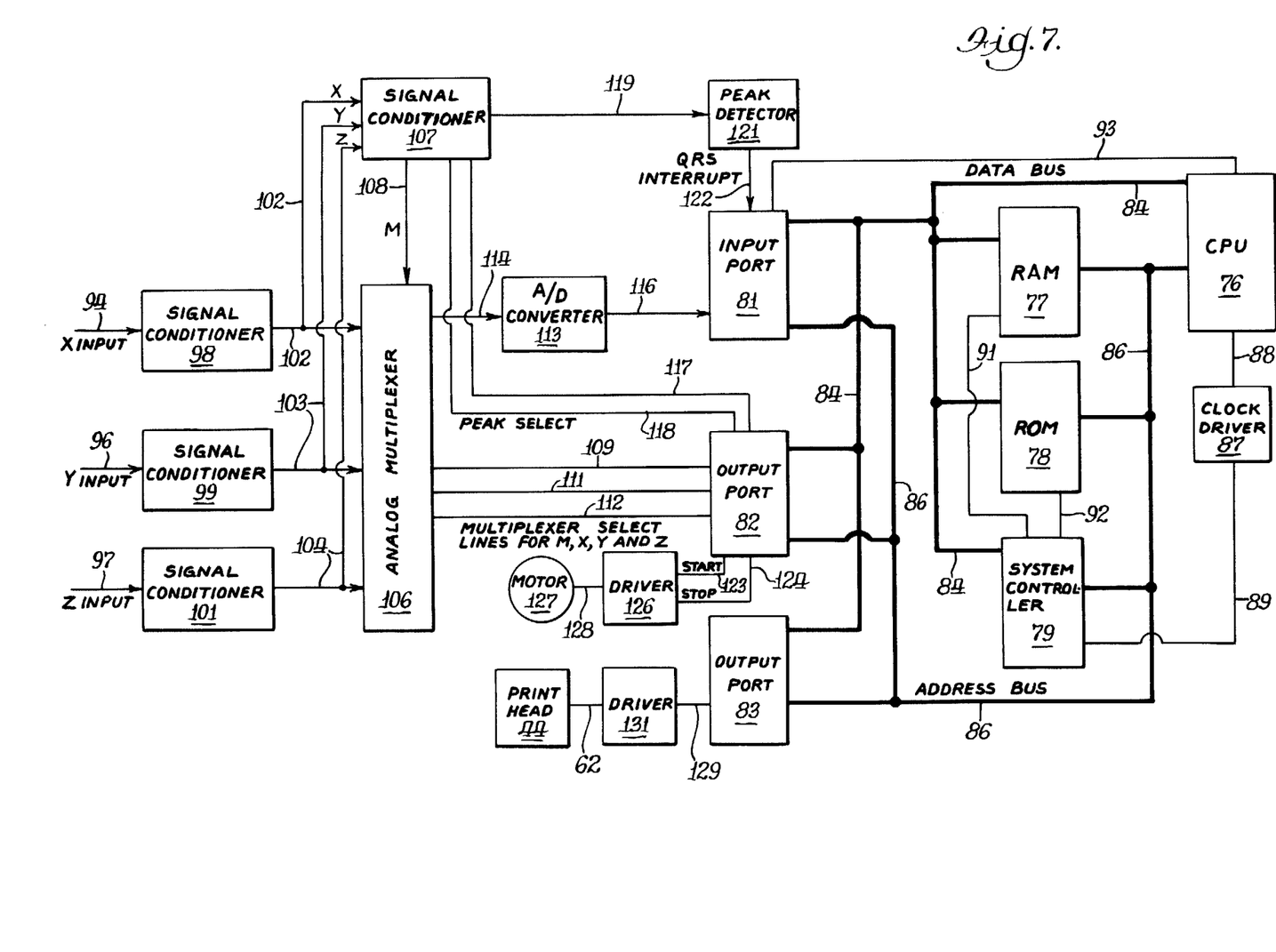
FIG. 7 is a schematic block diagram illustrating the basic features of the electronic circuitry of the data plotter of the preferred embodiment of the present invention.

FIG. 7 is the basic electrical schematic block diagram of the microcomputer and associated input and output circuitry for the data plotter of the present invention. A general purpose eight bit digital computer central processing unit (CPU) 76, such as the previously identified Intel Corporation Model No. 8080 microprocessor, is connected to a random access memory (RAM) 77, a read-only memory (ROM) 78, a system controller 79, an input port or latch and buffer unit 81 and similar output ports 82 and 83 through an eight bit or line bidirectional data bus 84 and a sixteen bit address bus 86, all of these microcomputer elements comprising integrated circuit devices well-known in the art and described in detail in the Intel Corporation 8080 Microcomputer System Manual. The data bus 84 provides bidirectional communication between the CPU 76, the RAM 77 and ports 81, 82 and 83 for instructions and data transfers. A clock driver 87 is connected to the CPU 76 and to the system controller 79 through lines 88 and 89, while the system controller 79 is connected to the RAM 77 and to the ROM 79 through lines 91 and 92, respectively. Input port 81 is connected to CPU 76 through lines 93 for a purpose to be described.

An X input line 94, a Y input line 96 and a Z input line 97 are connected, along with the input circuitry to the pen motors 24, 26 and 27, to three substantially mutually perpendicular attachments to the body whose vector heart potentials are to be monitored. Inputs 94, 96 and 97 are respectively connected to identical known signal conditioners 98, 99 and 101, comprising amplifiers and filters, these signal conditioners being in turn connected, by means of lines 102, 103 and 104, to a known three-to-one analog multiplexer 106 and to another similar signal conditioner 107. The signal conditioner 107 supplies to analog multiplexer 106 the computed signals corresponding to the vector magnitude, designated herein by "M", through a line 108.

In response to control signals furnished through output port 82 to a set of three multiplexer select lines 109, 111 and 112, the analog multiplexer 106 selectively supplies to a known analog to digital (A/D) converter 113, through eight bit lines 114, either the X, Y, Z or M signals. The A/D converter 113 supplies the selected signals to the input port 81 through eight bit lines 116 for entry into the RAM 77. Truncation of the data furnished to the A/D converter 113 is automatically achieved by dropping the least significant bits over eight.

The present invention comprises means for selecting a time sample of X, Y and Z input data signals. For this purpose, CPU 76 furnishes control signals through output port 82 to a pair of peak select lines 117, 118 instructing the signal conditioner 107 which one of the X, Y or Z input signals are to be examined. The examined signals are furnished through lines 119 to a peak detector 121, which responds to the R portion of the examined signal to provide a QRS interrupt signal on a line 122 to input port 81 when requested by CPU 76 in response to an interrupt request signal furnished on line 93. The QRS interrupt signal, which is supplied to the CPU, sets a flag in the data stream furnished by the A/D converter 113, which previously has been simultaneously supplying X, Y, Z and M data signals to input port 81 for destructive read-in entry into RAM 77.

Output port 82 is connected through a start line 123 and a stop line 124 to a known driver 126 operable to control a motor 127, through control lines 128, for regulating the substantially continuous movement of the paper 32. Output port 83 is connected through to lines 129 to a driver 131 operable to supply appropriate electrical voltages through lines 62 to the print head 44 for selectively actuating or energizing its printing elements in accordance with microprocessor control.

In the preferred embodiment of the present invention, RAM 77 stores the addressable working or variable data comprising 128 values of each of the X, Y, Z and M input signals. The approximate peak value of the data is marked by the flag furnished as a signal on QRS interrupt line 122, and, for each of the inputs, the memory contains 64 values or words symetrically positioned about this flagged peak.

ROM 78 stores the addressable program instructions executed by the CPU 76. The program of ROM instructions is generally set forth in the flow charts of FIGS. 8 through 13, which will now be described.

In the drawings, following conventional format, a rectangular box symbolizes an action, step or operation, a diamond-shaped box denotes a decision and the inverted trapezoidal boxes denote input and output functions. The loops or steps are connected at points denoted by circles containing reference letters.

Figure 8:
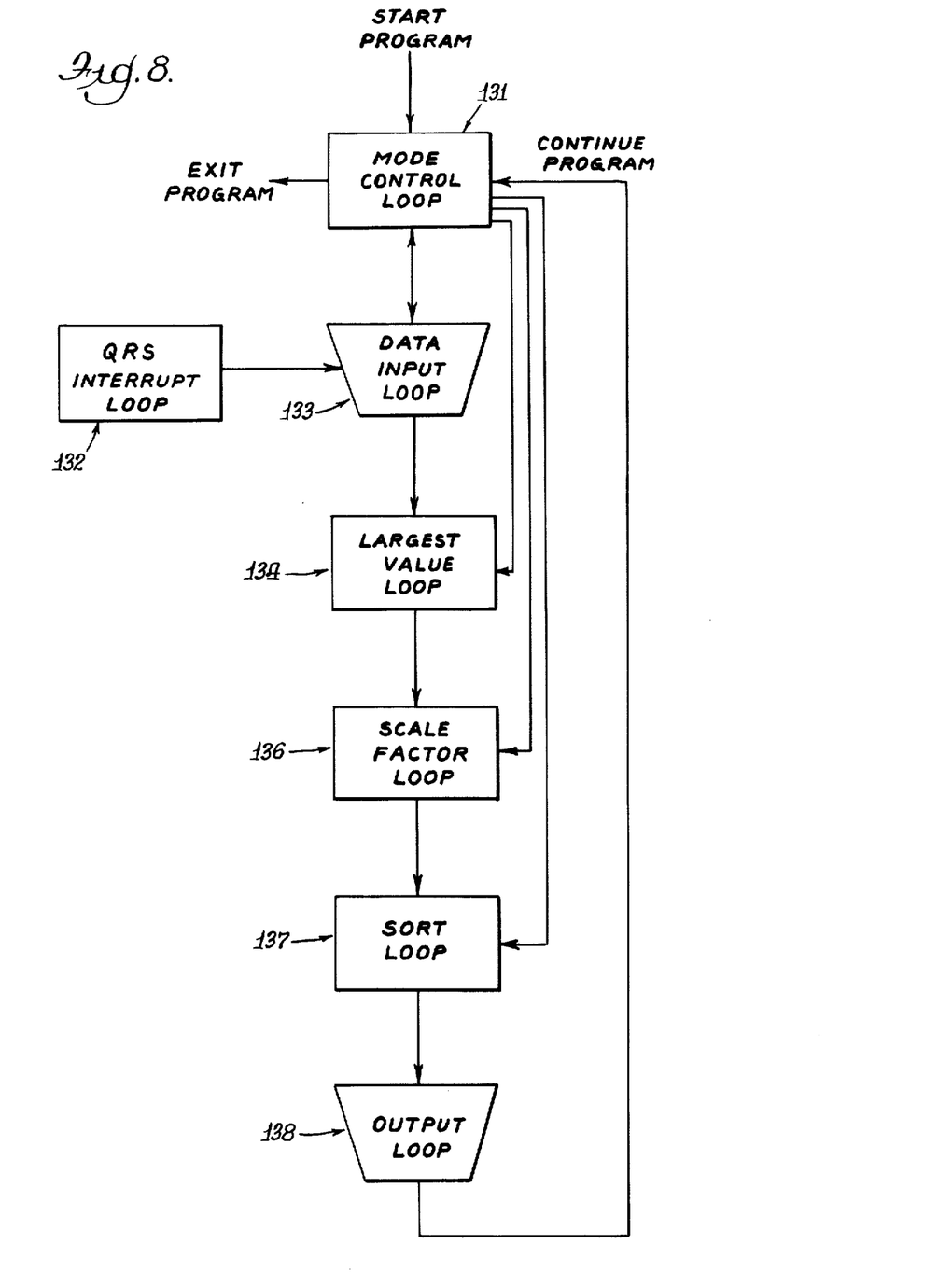
FIG. 8 is a basic flow chart of the microprocessor program.
Figure 9:
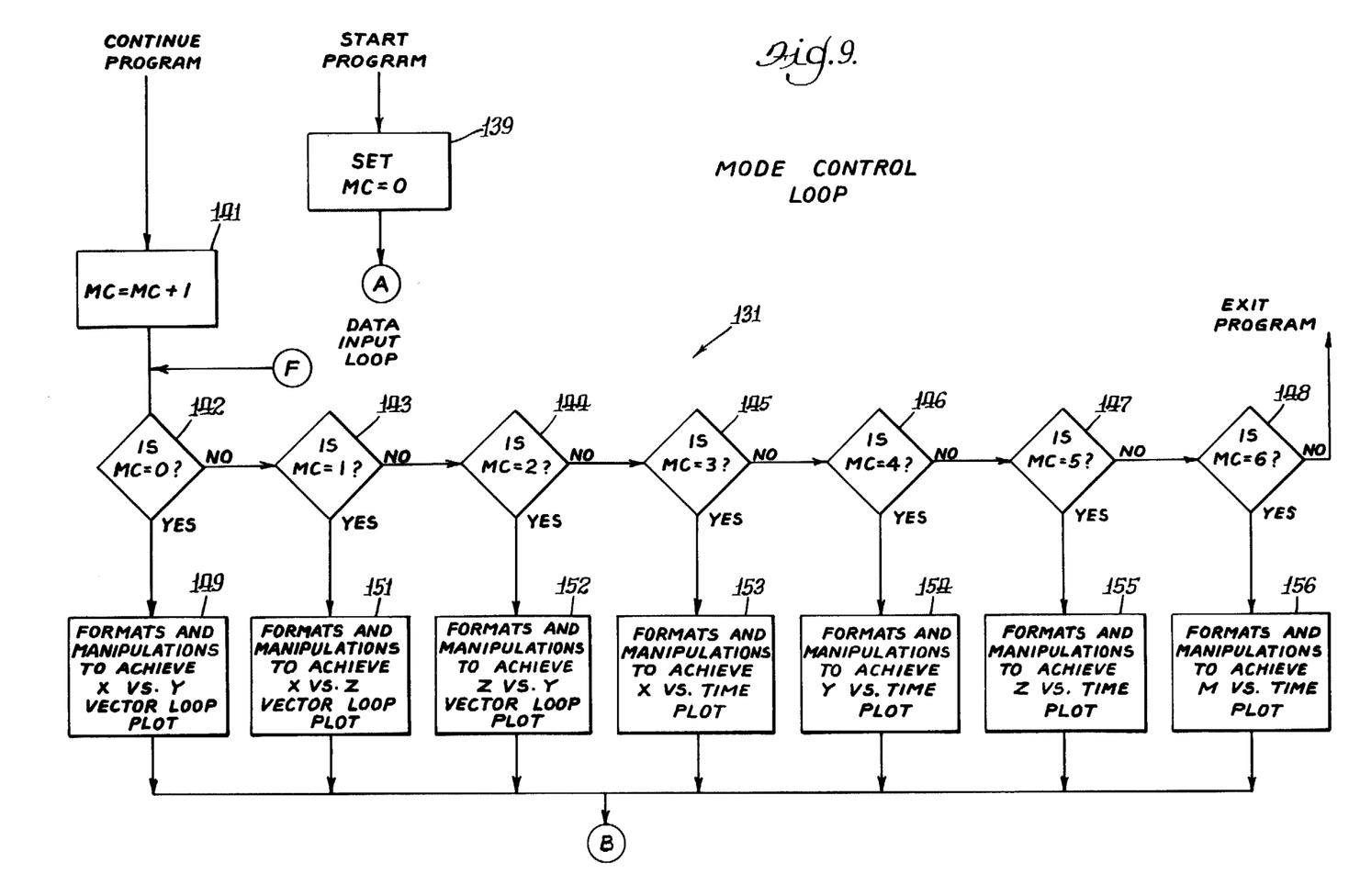
FIGS. 9 through 13 are additional flow charts illustrating in further detail aspects of the program generally diagrammed in FIG. 8.

With reference to FIG. 8, which is a flow chart illustrating the basic features of the microprocessor program, the program begins and ends at a mode control loop 131 diagrammed in further detail in FIG. 9. The mode control loop 131 governs the performance of various formats and manipulations for each of the plots of the vector loops 63, 64 and 66 and the derived time functions 67, 68, 69 and 71 which are shown in FIG. 3.

Figure 10:
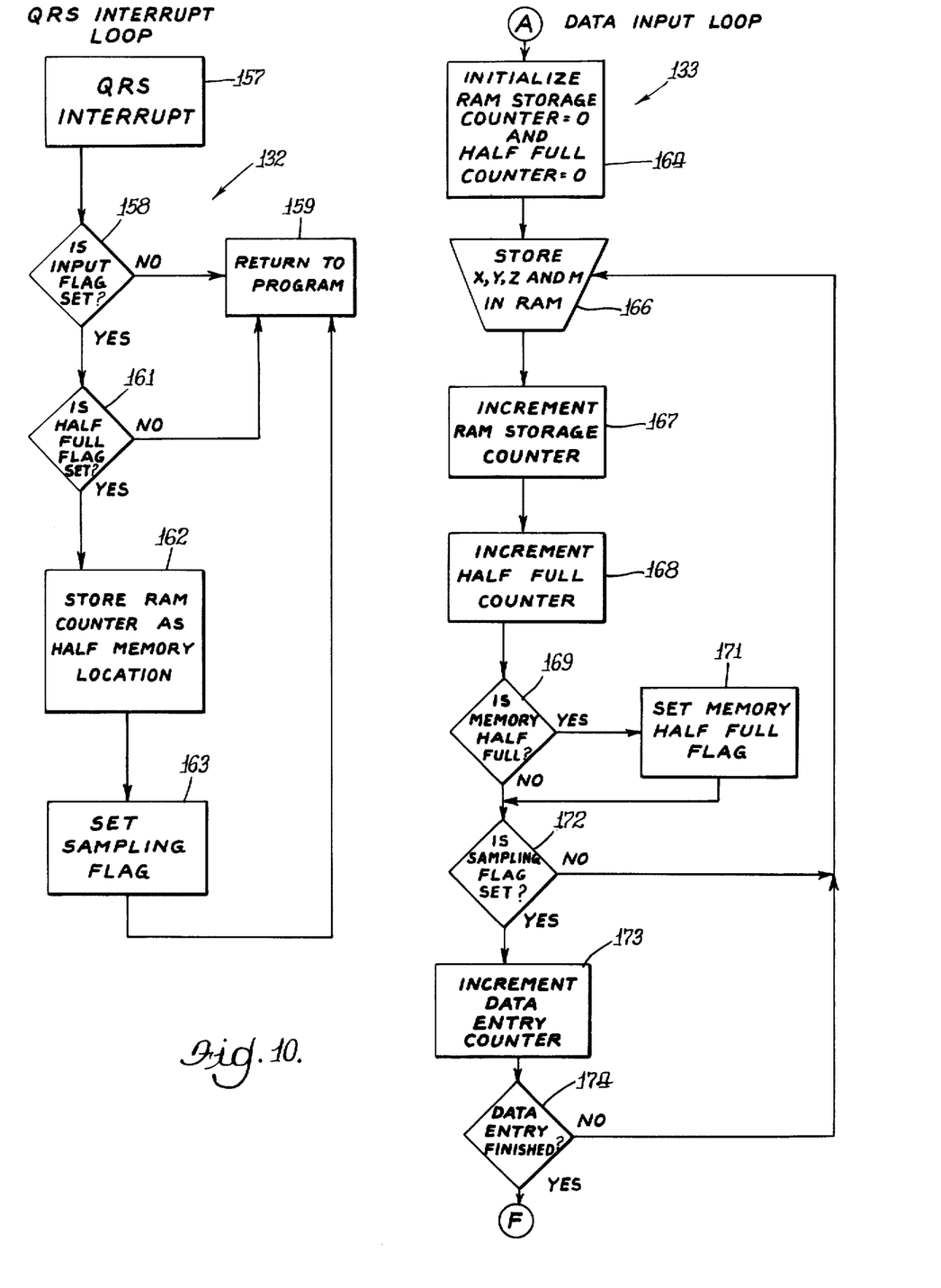

As also shown in FIG. 8, a QRS interrupt loop 132 and a data input loop 133, which are illustrated in detail in FIG. 10, provide means for selecting a time sample of the X, Y and Z time-variant analog scalar components of the three-dimensional vector data signals and also provide means for storing the sampled data as time sequential series of values.

Figure 11:
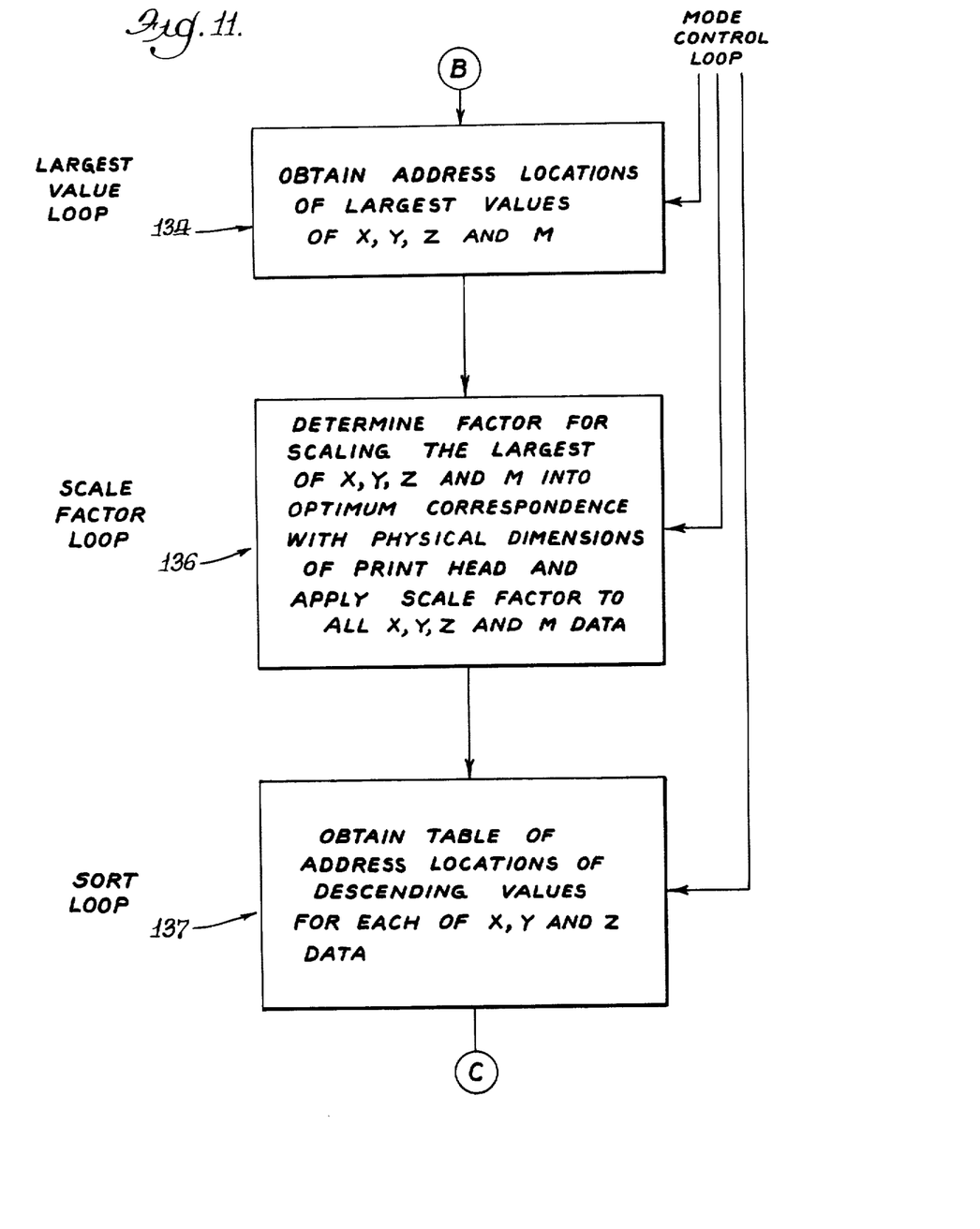

A largest value loop 134, a scale factor loop 136 and a sort loop 137, shown generally in FIG. 8, are illustrated in further detail in FIG. 11. These loops or steps govern means for converting the analog scalar components into integer data form in correspondence with the 128 printing elements of the print head 44, means for arranging each independent data set (such as the X input data of the numerical example of FIGS. 4 through 6) as a numerically ordered series of values and sorting means for incrementally varying each ordered data series and for identifying for each value in each series the time-associated values of stored data in the dependent data set (such as the Y data in the numerical example).

Figure 12:
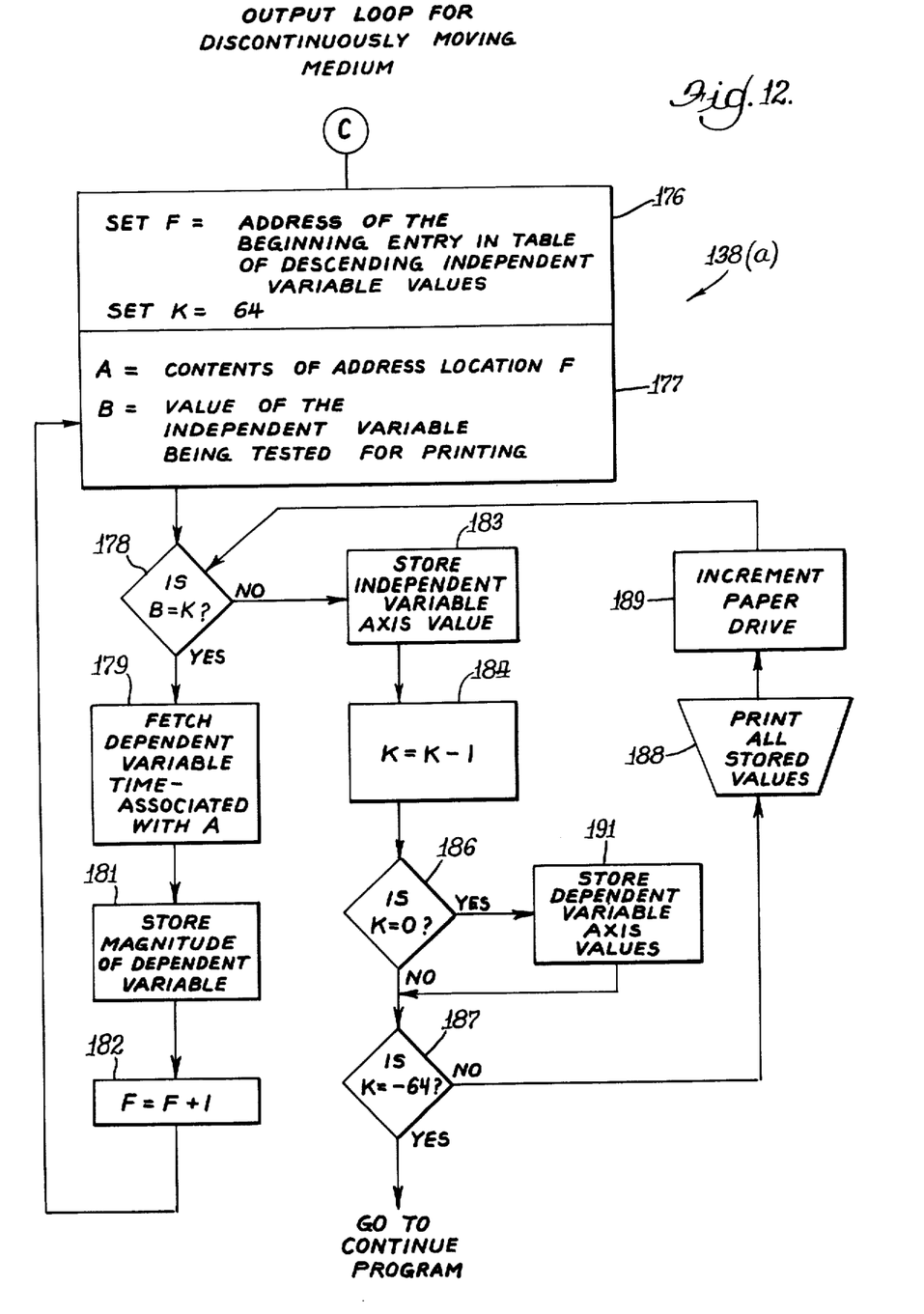
Figure 13:
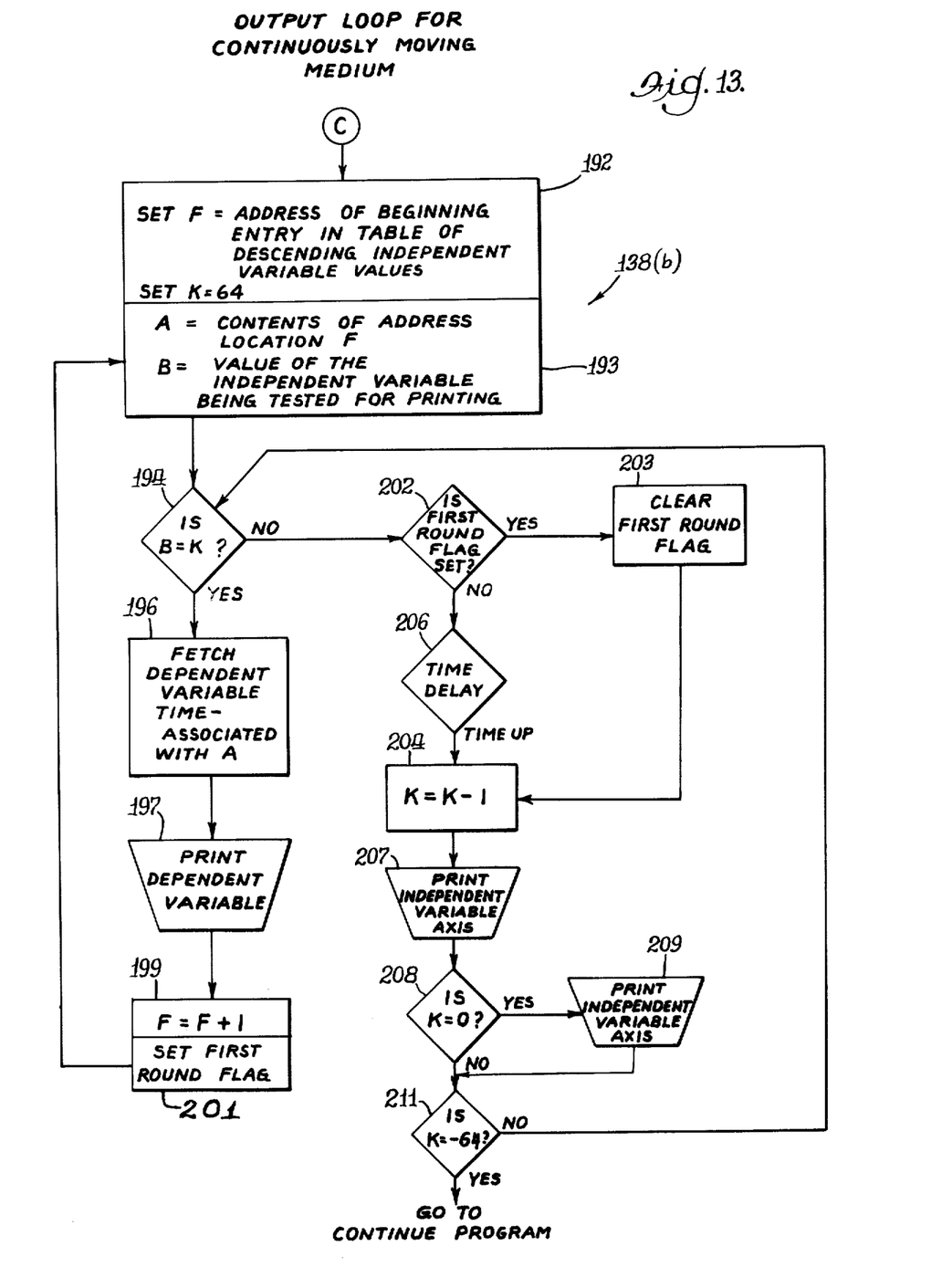

An output loop 138 contains the instructions for actuating the printing elements corresponding to the derived integer data on the moving paper or recording medium 32. An output loop generally illustrated by reference numeral 138(a) is illustrated in FIG. 12 for a discontinuously moving strip chart medium 32, while an alternate output loop indicated by reference numeral 138(b) is shown in FIG. 13 for a continuously moving medium.

With reference to FIG. 9, when the program is started, a mode control counter, designated "MC", is initially set at zero by an operation or step 139, and the program proceeds to the data input loop 133 (FIG. 10). After the output loop 138 (FIG. 8) is terminated, the program is continued through an action or step 141 which increments the mode control counter by one. A series of decisions 142 through 148 test the value of the mode control counter and require termination of the program if the counter value is 7 or above. For MC values from 0 through 6, the decisions 142 through 148 sequentially initiate routines 149 through 156, respectively, which generally symbolize the formats and manipulations for the identification of the X versus Y, the X versus Z and the Z versus Y two-dimensional data pairs for vector loop plots and the X versus time, the Y versus time, the Z versus time and the vector magnitude (M) versus time derived function plots. The vector format routines 149, 151 and 152 govern operations by the largest value loop 134, the scale factor loop 136 and the sort loop 137, while the derived time function routines 153, 154, 155 and 156 designate only the manipulations by the largest value loop and the scale factor loop.

As noted earlier, the QRS interrupt loop 132 and the data input loop 133 generally illustrated in FIG. 10 have as their purpose the selection of a time sample of ventricular QRS complex data input signals from which the vector loops and the other plotted time functions can be derived. Once the data values for the X, Y, Z and M variables encompassing one QRS complex are stored in RAM 77, the data input loop 133 will be skipped until all of the vector and time function plots have been printed.

In response to the presence of a QRS interrupt signal on line 122 represented by an operation 157 in FIG. 10, a decision 158 determines whether the microprocessor system is in an analysis mode or, alternatively, is in condition for receiving data. As noted earlier, input port 81 receives an interrupt request signal from CPU 76 on line 93. If the input flag is not set, indicating that the system is in an analysis mode, a step 159 requires that the program be resumed. If, however, the input flag is set, indicating that the system is receptive of data, a subsequest decision 161 questions whether RAM 77 is at least one-half full of data by checking whether a half full flag is set (by an operation to be described). If, however, RAM 77 is half full of data, an operation or action 162 requires that the current RAM counter or address be stored as a half memory location. Since the QRS interrupt is produced in response to the peak of the R portion of the QRS complex, the portion of maximum diagnostic interest, the peak value of the signal examined by signal conditioner 107 is marked by a step 162. Signal conditioner 107 is controlled to selectively examine either the X, Y, Z or M data by control signals on peak select lines 117 and 118 generated by manual or automatically programmed operation of a suitable switching means (not shown). Thereafter, an operation 163 sets a sampling flag for a purpose to be described.

As also shown in FIG. 10, an operation 164 initializes at zero both a RAM storage counter and a half full counter. An input step 166 illustrates the simultaneous storage of the X, Y, Z and M data into RAM 77, and operations or actions 167 and 168 require that the RAM storage counter and the half full counter be incremented. If the memory is half full, a decision 169 requires that the memory half full flag be set by an operation 171. Thereafter, a decision 172 questions whether the sampling flag has been set by operation 163 as previously described. If not, the input step 166 continues the storage of data into RAM 77. If the sampling flag has been set, an operation or action 173 increments a data entry counter, which is tested at a decision 174, to determine whether data entry has been completed. Since the RAM 77 should contain 64 values of X, Y, Z and M data symetrically positioned about the peak flag, decision 174 insures that the RAM should receive 64 additional samples counted from the half memory location stored by step 162, the memory half full flag indicating that 64 data samples have already been stored. When the data acquisition has been accomplished, the loops diagrammed in FIG. 11 are then entered.

The largest value loop 134 (FIG. 11) obtains the address locations of the largest values of X, Y, Z and M. Address locations instead of actual data values are obtained since any data value is readily obtainable simply by addressing RAM 77 at the desired address location. This routine 134 is well-known in the art, and is accomplished simply by comparing each data element in turn with its neighbor. If the data element is smaller than its neighbor, the value of the neighbor is used to replace the original element value. The process is repeated until no neighbor is found with a higher value, at which point the maximum value is obtained. The process is repeated for each of the sets of X, Y, Z and M data.

Thereafter, the scale factor loop 136, which comprises a well-known routine, determines a scale factor for scaling the largest of the X, Y, Z and M data into optimum correspondence with the physical dimensions of the print head 44, which, as noted earlier, preferably contains 128 printing elements. This scale factor is then applied to all of the X, Y, Z and M data so that new scaled data tables are generated.

The sort loop 137 then obtains, in a known manner, a table of address locations of descending values for each of the X, Y and Z data. This sorting procedure is not required for the M data, as governed by the mode control loop of FIG. 9. The sort loop or routine 137 rearranges each independent variable data set as a numerically ordered series of values similar to decreasing series of X values found in the chart appearing on page 11 for the previously described numerical example of FIGS. 4, 5 and 6. As illustrated by that example, the time-associated values of stored data in the dependent data set will be identified for each ordered value in the associated independent variable data set. Because of the operation of the scale factor loop 136, the maximum value of the independent variable cannot exceed 64, and the minimum negative value cannot drop below $-64$, resulting in a field of 128 bits or less.

FIGS. 12 and 13 illustrate alternate means for selectively actuating the printing elements of the print head 44 to register or plot dots on the paper 32, FIG. 12 showing an output loop 138($a$) for a discontinuously moving medium, and FIG. 13 illustrating an output loop 138($b$) for a continuously moving medium and producing an output similar to that shown in FIG. 3.

In general, for each two-dimensional data pair comprising an independent and an associated dependent data set, beginning at the maximum positive value of the independent variable and proceeding downward, each value of the independent variable data which has one or more time-associated values of the dependent variable data causes the dependent variable data to be registered or plotted on the paper 32 by the selectively actuable elements of the print head 44. The derived time function plots are sequentially generated in a similar manner. The printing elements of print head 44 are also actuated for plotting independent and dependent variable axes for reference. In addition, stored alphanumeric indicia such as patient indentification data could also be plotted in a known manner, but such character data plots are omitted from this disclosure for simplification.

With reference to FIG. 12, a step 176 sets a flag, denoted "F", equal to the address of the beginning entry in the table of descending independent variable values, that table having been previously generated by the sort loop 137. A second flag, "K", is set equal to 64. Another operation or action 177 sets a flag "A" equal to the contents of the address location "F", that is, equal to the beginning entry in the table of descending independent variable values. In addition, a counter "B" is set equal to the value of the independent variable being tested for printing or fit.

At a decision 178, the identity between "B", the value of the independent variable being tested for printing, and the current value of "K" is questioned. If "B" is equal to "K", indicating a fit condition, an action 179 requires that the dependent variable time-associated with the value of counter "A" be fetched. The magnitude of this fetched dependent variable is stored by a step 181, an operation 182 increments the value of the "F" counter by one, and this fit-testing loop is re-entered. When the derived time function data sets are plotted, the operation 179 similarly fetches or obtains the values of derived data time-associated with the current independent variable value.

If the value of the independent variable being tested for printing is not equal to the current value of "K", an action 183 requires storage of the independent variable axis value, a step 184 decreases the value of the "K" counter by one, and decisions 186 and 187 then test the equivalence of the current value of K to 0 and $-64$, respectively.

If the current value of "K" is neither 0 nor $-64$, all of the stored values are printed by an output operation 188, the discontinuous paper drive is incremented by an action 189 and the output loop is continued through the decision 178.

When the value of "K" reaches 0, an operation 191 requires storage of the dependent variable axis values for subsequent registration or plotting thereof. When the value of "K" reaches $-64$, the output loop 138($a$) is exited, and the program is continued through operation 141 of the mode control loop illustrated in FIG. 9.

It should be noted that operation of the output loop 138(a) occurs after the sampled analog scalar data are recorded by the pens 21, 22 and 23, and the vector loops and derived time functions are sequentially plotted.

FIG. 13 illustrates the output loop 138(b) for a continuously moving medium 32. Operations 192 and 193 perform the identical functions as operations 176 and 177, respectively, for the output loop 138(a) of FIG. 12. A decision 194 ascertains the identity between the value of the independent variable being tested for printing and the value of "K", initially set at 64. If there is an identity or fit condition, the dependent variable time-associated with the beginning entry in the table of descending independent variable values is fetched or obtained by an operation or action 196, and this dependent variable is immediately printed by an output action 197. Thereafter, a step 198 increments the "F" counter by one, and an action 201 sets a first round flag. The operation 196 obtains values of derived data time-associated with the current independent variable value for sequential plotting of the derived data sets.

In the output loop 138(b), each output cycle is divided into two identical time periods, one for printing of dependent variable data (called the "first round") and the other for printing of axis values. In the event there are two independent variable values time-associated with a value of the independent variable being tested for printing, the axis printing will be skipped. If there are more than two independent variable data values, a skewing of the data plotting will be experienced until the condition is relieved. However, this skewing effect will not adversely effect the diagnostic value of the plotted vector loops. If there is no fit or printing, only the axis values will be printed.

When "B", the value of the independent variable being tested for printing, is found to be unequal to 64, a decision 202 will inquire whether the first round flag has been set by operation 201. If so, a step 203 will clear the first round flag and the value of the counter "K" will be decremented by one at an action 204. If, however, the first round flag has not been set, a time delay will be required by time delay means comprising a decision 206, the delay being equal to the printing time consumed by the output operation 197. The purpose of this time delay means is to schedule actuation of the printing elements corresponding to the identified time-associated dependent variable data as the paper 32 moves in increments corresponding to value variations in the stored independent variable data, the microprocessor operations occurring far more rapidly than the paper movement. An output operation 207 thereafter requires printing of the independent variable axis value.

When the current value of the counter "K" is equal to 0, as determined by a decision 208, an output operation 209 requires printing of the dependent variable axis. When the current value of the counter "K" reaches −64, as determined by a decision 211, the program is continued through operation 141 of the mode control loop illustrated in FIG. 9, but until then, the output loop is continued through decision 194.

It is thought that this invention and many of its attendant advantages will be understood from the foregoing description, and it is apparent that various changes may be made in the form, construction and arrangement of its component parts without departing from the spirit and scope of the invention or sacrificing all of its material advantages, the form described being merely a preferred embodiment thereof.

The embodiments of the invention in which an exclusive property or privilege is claimed are as follows:

1. In a multi-channel chart recorder receptive of and operable to record first and second timevariant analog scalar components of ventricular QRS complex input vector data signals on a moving recording medium, a data plotter for printing QRS vector loops comprising:

stationary printing means having a series of selectively actuable printing elements spaced transversely to the longitudinal axis of said medium;

means for mounting said printing means on the recorder in printing contact with said medium;

means for selecting a time sample of said data signals;

means for storing each of said first and second data for said selected sample as a time sequential series of values;

means for converting said first and second analog scalar components into integer data form in correspondence with said elements;

means for arranging said stored first data as a numerically ordered series of values;

sorting means for incrementally varying said ordered first data and for identifying for each value thereof the time-associated values of said stored second data; and means for actuating said printing elements corresponding to said identified second data as said medium moves in increments corresponding to value variations of said stored first data.

2. The plotter of claim 1 wherein said selecting means comprises means for identifying the peak of the R portion of a selected one of said scalar components.

3. The plotter of claim 1 wherein said medium is continuously moving, and time delay means for scheduling actuation of said printing elements corresponding to said identified second data as said medium moves in increments corresponding to value variations of said stored first data.

4. In a multi-channel chart recorder receptive of and operable to record first, second and third time-variant analog scalar components of three-dimensional input vector data signals on a continuously moving recording medium, a data plotter comprising:

stationary printing means having a series of selectively actuable printing elements spaced transversely to the longitudinal axis of said medium;

means for mounting said printing means on the recorder in printing contact with said medium;

means for selecting a time sample of said data signals;

means for storing each of said first, second and third data for said selected sample as a time sequential series of values;

means for converting said first, second and third analog scalar components into integer data form in correspondence with said elements;

means for identifying from said stored first, second and third integer data three two-dimensional data pairs each comprising an independent and a dependent data set thereof;

means for arranging each independent data set as a numerically ordered series of values;

sorting means for incrementally varying each said ordered data series and for identifying for each value thereof the time-associated values of stored data in the dependent data set associated therewith; and means for sequentially plotting said identified dependent data sets as functions of their associated independent data sets comprising means for energizing said printing elements corresponding to said identified dependent data sets as said medium moves in increments corresponding to value variations in said independent data sets.

5. The plotter of claim 4 and means for actuating said printing elements for plotting reference axes corresponding to said independent and dependent data sets.

6. The data plotter of claim 4 wherein said printing means comprises a thermal print head having selectively energizable printing elements.

7. The data plotter of claim 4 wherein said mounting means comprises a spring for urging said head into printing contact with said medium.

8. The data plotter of claim 4 and
means for deriving a time-variant data set from at least one of said components of said sampled vector data signals;
means for storing said derived data set as a time sequential series of values;
means for converting said derived data set into integer data form in correspondence with said elements; and
means for actuating said printing elements corresponding to said derived integer data for printing on said moving medium in order to plot said derived data set.

9. The data plotter of claim 8 wherein said deriving means is operable to compute the time-variant magnitude of said sampled vector data signals.

10. The data plotter of claim 4 wherein said recorder is operable to record first, second and third time-variant analog scalar components of ventricular QRS complex data signals and said data plotter is operable to print QRS vector loops for the transverse, sagittal and frontal planes each corresponding to one of said data pairs.

11. The data plotter of claim 10 wherein said selecting means comprises means for identifying the peak of the R portion of a selected one of said scalar components.

12. The data plotter of claim 10 wherein said medium is continuously moving, and time delay means for scheduling actuation of said printing elements corresponding to said identified second data as said medium moves in increments corresponding to value variations of said stored first data.

13. The data plotter of claim 10 and
means for deriving a time-variant data set from each of said components of said sampled vector data signals;
means for deriving the time-variant magnitude of said sampled vector data signals;
means for storing each said derived data set as a time sequential series of values;
means for converting each said derived data set into integer data form in correspondence with said elements;
means for actuating said printing elements corresponding to said derived integer data for printing on said moving medium in order to sequentially plot said derived data sets; and
means for actuating said printing elements for plotting reference axes for each of said vector loops and said derived data sets.

* * * * *